(12) United States Patent
Haverkost et al.

(10) Patent No.: US 7,235,095 B2
(45) Date of Patent: Jun. 26, 2007

(54) METHOD AND SYSTEM FOR DEPLOYING MULTI-PART ENDOLUMINAL DEVICES

(75) Inventors: Patrick A. Haverkost, Brooklyn Center, MN (US); Paul F. Chouinard, Maple Grove, MN (US); James Weldon, Roslindale, MA (US); Karen McDonald, North Billerica, MA (US); Wade M. Johnson, Minneapolis, MN (US); Juan Carlos Parodi, Capital Federal (AR)

(73) Assignee: Scimed Life Systems, Inc., Maple Grove, MN (US)

( * ) Notice: Subject to any disclaimer, the term of this patent is extended or adjusted under 35 U.S.C. 154(b) by 66 days.

(21) Appl. No.: 10/080,791

(22) Filed: Feb. 22, 2002

(65) Prior Publication Data

US 2003/0163188 A1    Aug. 28, 2003

(51) Int. Cl.
*A61F 2/06* (2006.01)
*A61M 29/00* (2006.01)

(52) U.S. Cl. ............... 623/1.12; 606/108; 606/191
(58) Field of Classification Search ............ 606/1, 606/108, 151, 191–200, 213; 623/1.11, 1.16, 623/1.35, 1.36, 1.44; 604/104–109
See application file for complete search history.

(56) References Cited

U.S. PATENT DOCUMENTS

| 4,140,126 | A |   | 2/1979  | Choudhury |
| 4,732,152 | A |   | 3/1988  | Wallstén et al. |
| 4,787,899 | A | * | 11/1988 | Lazarus ............... 623/1.11 |
| 4,950,227 | A |   | 8/1990  | Savin et al. |
| 5,078,720 | A | * | 1/1992  | Burton et al. ............ 606/108 |
| 5,122,136 | A |   | 6/1992  | Guglielmi et al. |
| 5,158,548 | A | * | 10/1992 | Lau et al. ............... 606/194 |
| 5,201,757 | A | * | 4/1993  | Heyn et al. ............. 606/198 |
| 5,354,295 | A |   | 10/1994 | Guglielmi et al. |
| 5,415,664 | A |   | 5/1995  | Pinchuk |

(Continued)

FOREIGN PATENT DOCUMENTS

EP    0 637 454    2/1995

(Continued)

OTHER PUBLICATIONS

International Search Report for Corresponding PCT/US03/04832, Mail date Aug. 5, 2003.

(Continued)

*Primary Examiner*—Glenn K. Dawson
(74) *Attorney, Agent, or Firm*—RatnerPrestia

(57) ABSTRACT

A method for deployment of a multi-part endoluminal device includes deploying a first portion of the device sequentially from its distal end to its proximal end, then deploying a second portion of the device sequentially from its proximal end to its distal end so that its distal end overlaps the first portion proximal end. The system for deploying the endoluminal device includes a first introducer loaded with a first endoluminal device and adapted to deploy the first device sequentially from the distal end to the proximal end, and a second introducer loaded with a second endoluminal device and adapted to anchor the second endoluminal device proximal end while deploying the second endoluminal device sequentially from the proximal end to the distal end.

26 Claims, 7 Drawing Sheets

U.S. PATENT DOCUMENTS

| | | | |
|---|---|---|---|
| 5,445,646 A | | 8/1995 | Euteneuer et al. |
| 5,456,694 A | | 10/1995 | Marin et al. |
| 5,480,423 A | | 1/1996 | Ravenscroft et al. |
| 5,591,228 A | | 1/1997 | Edoga |
| 5,609,627 A | * | 3/1997 | Goicoechea et al. ........ 128/898 |
| 5,634,928 A | | 6/1997 | Fischell et al. |
| 5,662,675 A | | 9/1997 | Polanskyj Stockert et al. |
| 5,683,451 A | | 11/1997 | Lenker et al. |
| 5,690,644 A | * | 11/1997 | Yurek et al. ............... 623/1.11 |
| 5,800,526 A | | 9/1998 | Anderson et al. |
| 5,807,101 A | | 9/1998 | Scalzo |
| 5,817,101 A | * | 10/1998 | Fiedler ...................... 623/1.11 |
| 5,843,164 A | | 12/1998 | Frantzen et al. |
| 5,860,998 A | | 1/1999 | Robinson et al. |
| 5,980,533 A | | 11/1999 | Holman |
| 5,989,280 A | | 11/1999 | Euteneuer et al. |
| 6,042,589 A | | 3/2000 | Marianne |
| 6,102,942 A | | 8/2000 | Ahari |
| 6,168,610 B1 | | 1/2001 | Marin et al. |
| 6,183,443 B1 | | 2/2001 | Kratoska et al. |
| 6,290,710 B1 | | 9/2001 | Cryer et al. |
| 6,322,586 B1 | | 11/2001 | Monroe et al. |
| 6,468,244 B1 | | 10/2002 | Leone et al. |
| 6,544,223 B1 | | 4/2003 | Kokish |
| 6,613,075 B1 | | 9/2003 | Healy et al. |
| 2001/0044648 A1 | | 11/2001 | Wolinsky et al. |

FOREIGN PATENT DOCUMENTS

| | | |
|---|---|---|
| EP | 0 684 022 | 11/1995 |
| WO | WO 96/24308 | 8/1996 |
| WO | WO-98/09583 | 3/1998 |
| WO | WO 98/53761 | 12/1998 |
| WO | WO-99/47075 | 9/1999 |
| WO | WO 99/49812 | 10/1999 |
| WO | WO-01/10345 A1 | 2/2001 |

OTHER PUBLICATIONS

International Search Report for Corresponding PCT/US03/04662, Mail date Jul. 3, 2003.
U.S. Appl. No. 09/442,165, filed Nov. 16, 1999 to Choulnard et al.
U.S. Appl. No. 09/442,192, filed Nov. 16, 1999 to Zarbatany et al.
U.S. Appl. No. 09/574,418, filed May 19, 2000 to Sullivan et al.
U.S. Appl. No. 09/852,524, filed May 10, 2001 to Elliott.
U.S. Appl. No. 10/081,636, filed Feb. 22, 2002 to Thompson et al.
U.S. Appl. No. 10/081,641, filed Feb. 22, 2002 to Haverkost et al.
International Search Report for corresponding PCT/US03/04943, mailing date Aug. 5, 2003.
U.S. Appl. No. 10/080,791, filed Feb. 22, 2002 to Haverkost et al.
International Search Report for Corresponding PCT/US03/04662, dated Jul. 3, 2003.
International Search Report for Corresponding PCT/US03/04943, dated Aug. 5, 2003.
International Search Report for Corresponding PCT/US03/04832, dated Aug. 5, 2003.

* cited by examiner

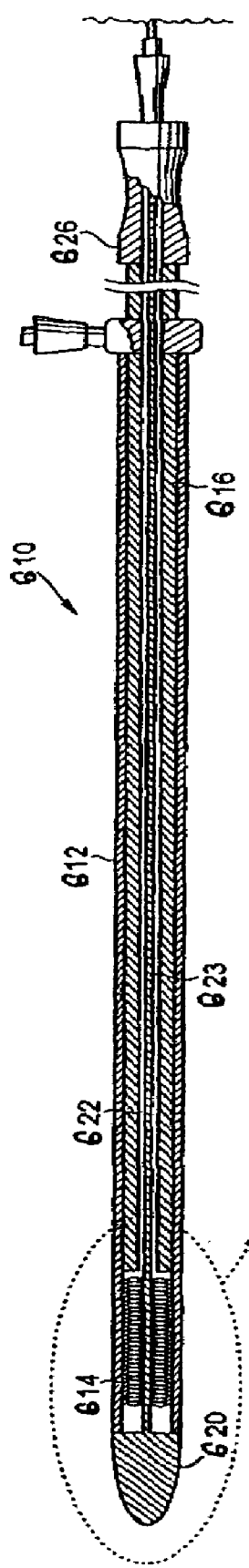
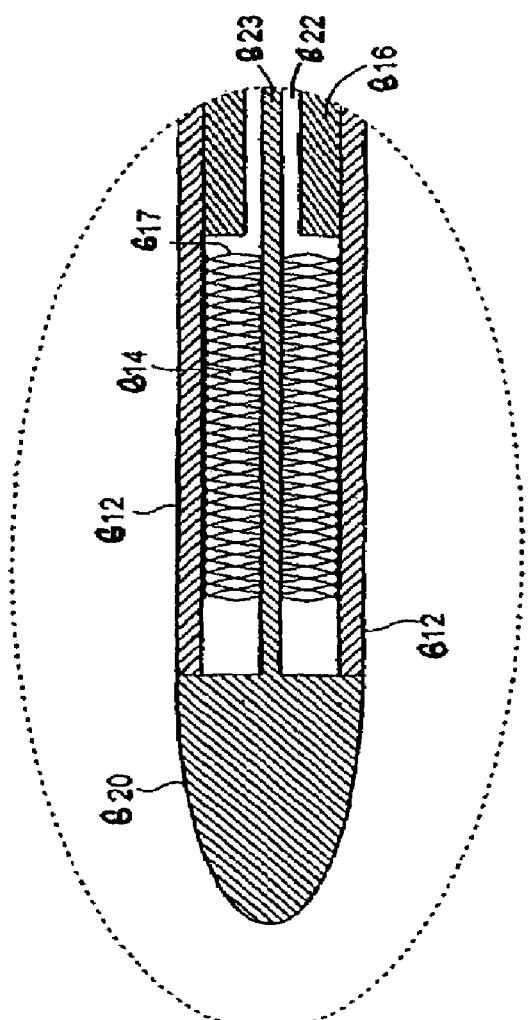
FIG. 6A
FIG. 6B

METHOD AND SYSTEM FOR DEPLOYING MULTI-PART ENDOLUMINAL DEVICES

TECHNICAL FIELD

This invention relates generally to endoluminal devices and, more specifically, to methods and apparatus for deploying endoluminal devices in body lumens.

BACKGROUND OF THE INVENTION

A stent is an elongated device used to support an intraluminal wall. In the case of a stenosis, a stent provides an unobstructed conduit through a body lumen in the area of the stenosis. Such a stent may also have a prosthetic graft layer of fabric or covering lining the inside and/or outside thereof. Such a covered stent is commonly referred to in the art as an intraluminal prosthesis, an endoluminal or endovascular graft (EVG), or a stent-graft. A stent-graft may be used, for example, to treat a vascular aneurysm by removing the pressure on a weakened part of an artery so as to reduce the risk of rupture. Other devices, such as filters, may have similar structures to stents and may be placed in a body lumen by similar methods. As used herein, the term "endoluminal device" refers to covered and uncovered stents, filters, and any other device that may be placed in a lumen. The term "stent" as used herein is a shorthand reference referring to a covered or uncovered stent.

Typically, an endoluminal device, such as a stent-graft deployed in a blood vessel at the site of a stenosis or aneurysm, is implanted endoluminally, i.e. by so-called "minimally invasive techniques" in which the device, restrained in a radially compressed configuration by a sheath or catheter, is delivered by a delivery system or "introducer" to the site where it is required. The introducer may enter the body from an access location outside the body, such as through the patient's skin, or by a "cut down" technique in which the entry blood vessel is exposed by minor surgical means. The term "proximal" as used herein refers to portions of the stent or delivery system relatively closer to the end of the delivery system extending outside of the body, whereas the term "distal" is used to refer to portions relatively farther from this outside end.

When the introducer has been threaded into the body lumen to the stent deployment location, the introducer is manipulated to cause the stent to be ejected from the surrounding sheath or catheter in which it is restrained (or alternatively the surrounding sheath or catheter is retracted from the stent), whereupon the stent expands to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

It is often important during endoluminal device delivery to ensure accurate placement of the device termini, particularly in intravascular deployment of multipart stents. Improper stent placement can prevent successful medical treatment. There is a particular need in the art to anchor the proximal end of a self-expanding stent while deploying the distal end, and also to provide accurate deployment of self-expanding stents in a way that prevents recoil of the endoluminal device upon release, which may adversely affect the accuracy of the device placement. Balloons are commonly used to anchor endoluminal devices during deployment, but the pressure of a balloon against a vessel wall may damage tissue, particularly if the vessel wall is already diseased. Thus, it is further desirable to anchor the proximal end of an endoluminal device while deploying the distal end without applying unnecessary force against the vessel wall.

In a procedure to repair an abdominal aortic aneurysm (AAA), use of a modular self-expanding stent involves accurate placement of a terminus of a first stent component in the abdominal aorta just below the renal arteries. A second stent component is then deployed in the first stent component and permitted to extend to a terminus in one of the iliac arteries. It is difficult, however, to ensure accurate placement of the iliac terminus of the second stent component. If the terminus is not placed far enough into the iliac, then the stent may be ineffective. If the terminus extends too far, it may interfere with blood flow in arteries branching from the iliac, such as the internal iliac artery. This problem also occurs in the deployment of multipart stents in other branched arteries. Thus, it is desirable to provide a way to ensure accurate deployment of all the termini of a multipart stent.

A large aortic aneurysm has an unpredictable anatomy. It can have a long or short neck, and a complex and tortuous configuration that extends down to the iliac arteries. In such cases, exact measurements of the aneurysm's neck, angulation, and anatomical lengths are crucial to a successful repair. Making these measurements accurately is labor and resource intensive, often requiring expensive tests such as angiograms, intravascular ultrasounds, and three-dimensional CT scans. Moreover, the tortuous nature of an AAA may prevent highly accurate measurements. The need for accurate sizing and placement of AAA endografts has led to a large number of custom-sized devices, which increases the manufacturing cost of the devices. Thus, it is desirable to provide a stent that can be accurately deployed without a need for complex calculations to estimate the required size of the stent and, furthermore, to provide bifurcated multipart devices that have a smaller number of sizes that can fit a larger number of subjects.

SUMMARY OF THE INVENTION

One aspect of the invention comprises a method for deployment of a multi-part endoluminal device in a distal location in a body lumen from a proximal location. The device comprises at least a first portion and a second portion, each portion having a distal end and a proximal end. The method comprises the steps of deploying the first portion in a body lumen by aligning the first portion distal end in a desired location and then deploying a remainder of the first portion including the first portion proximal end; and deploying the second portion in the body lumen by aligning and anchoring the second portion proximal end in a desired location and then deploying a remainder of the second portion including the second portion distal end in overlapping engagement with the first portion proximal end. The first portion is typically deployed sequentially from the distal end to the proximal end whereas the second portion is typically deployed from the proximal end to the distal end.

In one aspect of the invention, the first portion of the device comprises a modular bifurcated device having a main body portion with a distal end, a first stump, and a second stump, each stump having a proximal end, and the second portion of the device comprises at least one leg portion adapted to interface with the first stump. The method of deploying this device comprises deploying the main body portion in a body lumen by aligning the distal end in a desired location and deploying the remainder of the main body portion from the distal end to the first stump proximal end and second stump proximal end, and then deploying the leg portion with the leg portion distal end in overlapping engagement with the first stump proximal end. Where the bifurcated device is adapted to be deployed in an aorta and the leg portions are adapted to be deployed in an iliac artery, the desired location for the leg portion proximal end is typically distal of an internal iliac artery. A second leg portion having a distal end and a proximal end may then be deployed by aligning and anchoring the second leg portion proximal end in a desired location and then deploying a remainder of the second leg portion including the second leg portion distal end in overlapping engagement with the second stump proximal end. Deployment of the main body and first leg portion may typically be carried out from a first proximal access location while the second leg portion is typically carried out from a second proximal access location.

In another aspect of the invention, the bifurcated device further comprises a leg connector portion having a proximal end and a distal end and adapted to interface between one of the stumps and one of the leg portions. The method for deployment thus comprises, after deploying the main body portion, deploying the leg connector portion by aligning the leg connector distal end with one of the stump proximal ends and then deploying a remainder of the leg connector including the leg connector proximal end. The leg portion that interfaces with the leg connector is then deployed by aligning and anchoring the leg portion proximal end in a desired location and then deploying a remainder of the leg portion including the leg portion distal end in overlapping engagement with the leg connector proximal end.

The reverse deployment steps of deploying a device proximal end first, may comprise a number of specific substeps. For example, the substeps may include inserting an introducer into the body lumen, the introducer comprising a retrograde portion; an anterograde portion; a shaft having a distal tip; an inner sheath mounted concentrically over the shaft with the endoluminal device mounted concentrically over the inner sheath; and an anterograde sheath proximally attached to the shaft distal tip, mounted over the endoluminal device in the anterograde portion of the introducer, and axially moveable relative to the inner sheath. The method then comprises aligning the introducer in a deployment location; extending the shaft to distally advance the anterograde sheath to deploy at least a distal portion of the endoluminal device; and removing the introducer from the body lumen.

Yet another aspect of the invention comprises a system for deploying an endoluminal device, the system comprising a first introducer loaded with a first endoluminal device and a second introducer loaded with a second endoluminal device. The first introducer is adapted to deploy the first device sequentially from the distal end to the proximal end. The second endoluminal device has a distal end adapted to engage the first endoluminal device proximal end, and the second introducer is adapted to anchor the second endoluminal device proximal end while deploying the second endoluminal device sequentially from the proximal end to the distal end. The second endoluminal device distal end is typically adapted to be deployed radially within the first endoluminal device proximal end and to laterally overlap the first endoluminal device proximal end along a length of at least about 2 centimeters. In one embodiment, the first endoluminal device may comprise a bifurcated device having a main body portion with a distal end, and two stumps, each stump having a proximal end, where the second endoluminal device comprises a first leg portion adapted to interface with the first stump. The device may further comprise a leg connector and/or a second leg portion, and corresponding introducers.

The introducers for reverse deployment may comprise a shaft having a distal tip; an inner sheath mounted concentrically over the shaft; the endoluminal device mounted concentrically over the inner sheath, and an anterograde sheath attached distally to the distal tip, mounted over the endoluminal device in the anterograde portion of the introducer, and distally moveable relative to the inner sheath by moving the shaft.

It is to be understood that both the foregoing general description and the following detailed description are exemplary, but not restrictive, of the invention.

BRIEF DESCRIPTION OF THE DRAWING

The invention is best understood from the following detailed description when read in connection with the accompanying drawing, in which:

FIG. 6A depicts a longitudinal cross section of a standard introducer of the prior art.

FIG. 6B depicts a detailed longitudinal cross section of the encircled portion of FIG. 6A.

DETAILED DESCRIPTION OF THE INVENTION

The invention will next be illustrated with reference to the figures wherein the same numbers indicate similar elements in all figures. Such figures are intended to be illustrative rather than limiting and are included herewith to facilitate the explanation of the apparatus of the present invention.

Figure 1A:
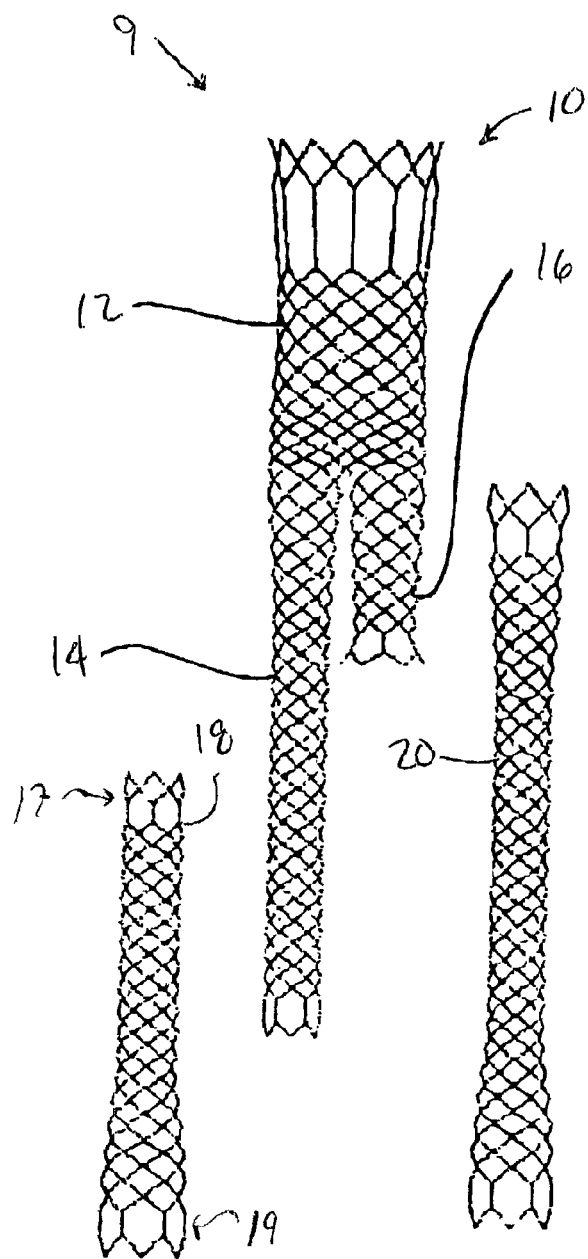
FIG. 1A is an illustration of an exemplary three-part endoluminal device of this invention in an unassembled configuration.
Figure 1B:
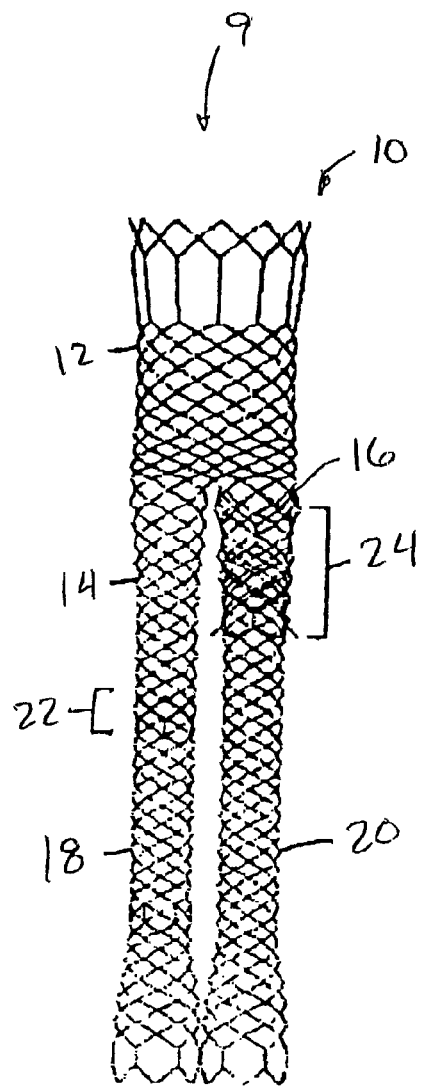
FIG. 1B is an illustration of the device of FIG. 1A in an assembled configuration.

Referring now to FIGS. 1A and 1B, there is shown an exemplary three-part prosthesis 9 prior to and after deployment by the method of this invention, respectively. The unassembled three-part prosthesis shown in FIG. 1A comprises a bifurcated segment 10 comprising a main body 12, a first stump 14 and a second stump 16; a first leg segment 18; and a second leg segment 20. First stump and second stump may be of the same length or of different lengths, as shown in FIGS. 1A and 1B. Although stump 14 is shown longer than stump 16, the relationship may be reversed. When assembled, first leg segment 18 overlaps first stump 14 in a first overlap 22 and second leg segment 20 overlaps second stump 16 in a second overlap 24.

First leg segment 18 and second leg segment 20 are preferably self expanding and sized to exert sufficient radial pressure on the interior of first stump 14 and second stump 16, respectively, to provide a seal with strength sufficient to prevent a medically unacceptable amount of leakage. The amount of radial pressure necessary to satisfy this condition depends on a variety of factors, such as the material used to make the stent graft, the environment into which the stent is being deployed, and the amount of overlap between the leg segments and their corresponding stumps. The components of the device are preferably designed to ensure at least a 2 cm overlap. Beyond this, it may be desirable to minimize overlap to maximize stent flexibility. Methods and structures for varying stent flexibility and radial strength are known in the art, such as described in U.S. patent application Ser. No. 09/442,192, filed Nov. 16, 1999, by Zarbatany et al., and incorporated herein by reference.

Figure 2A:
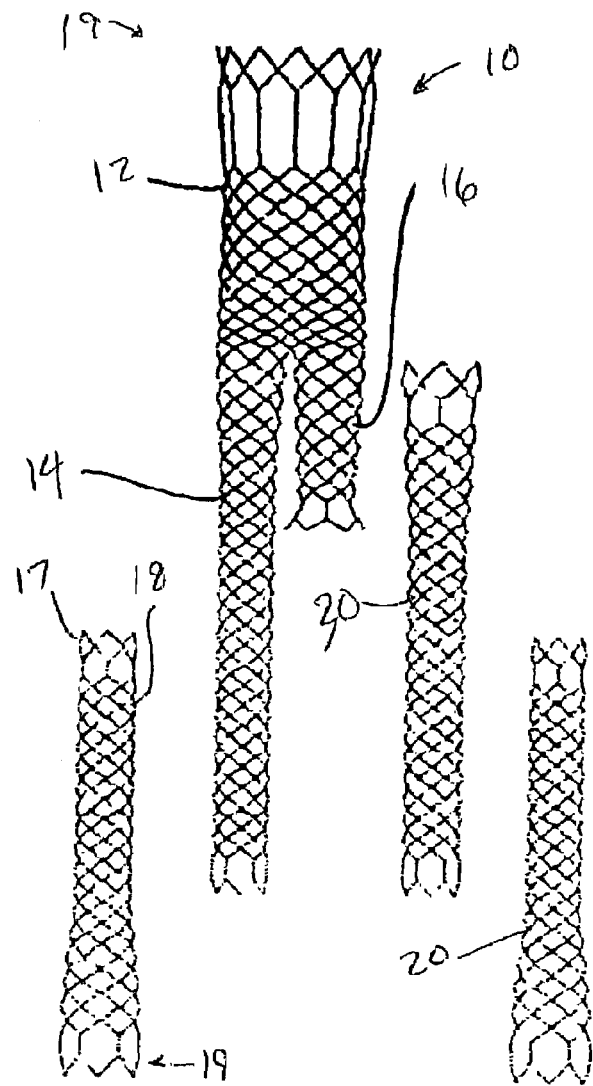
FIG. 2A is an illustration of an exemplary four-part endoluminal device of this invention in an unassembled configuration.

The prosthesis components typically comprises a stent made of a biocompatible material known in the art, such as stainless steel or nitinol, having any of the various architectures known in the art, such as but not limited to braided and/or wound (zig-zag, hexagonal, etc.) or laser or otherwise cut tube architectures. A preferred embodiment shown in FIGS. 1A and 2A is a hybrid of braided wire construction and wound construction, such as is described in U.S. patent application Ser. No. 09/442,165, filed Nov. 16, 1999, by Chouinard and Haverkost, and incorporated herein by reference. The stent typically supports, either as an inside lining, outside covering or both, a graft constructed from any of a variety of biocompatible materials known in the art. Various bonding agents may be used, in addition to radial pressure, to seal the components of the graft together. For purposes of clarity, the figures herein do not show the graft materials.

Figure 2B:
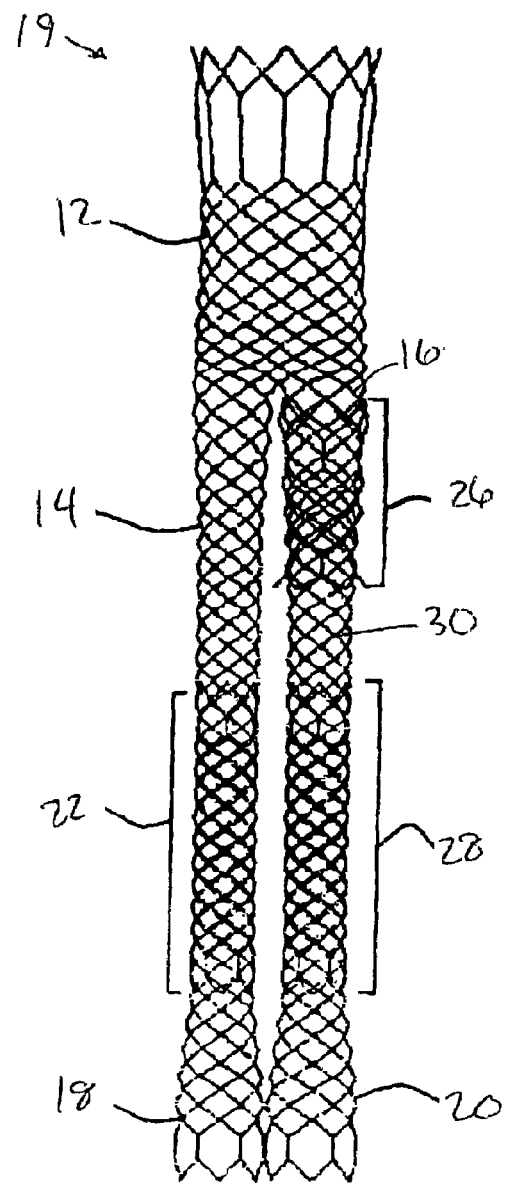
FIG. 2B is an illustration of the device of FIG. 2A in an assembled configuration.

FIGS. 2A and 2B show an exemplary four-part prosthesis 19 prior to and after deployment by the method of this invention. The main body 12, first leg segment 18 and second leg segment 20 of the four-part prosthesis are similar as for the three-part prosthesis, but the four-part prosthesis also comprises an additional leg connector segment 30 as shown in FIG. 2A. The assembled configuration shown in FIG. 2B comprises first leg segment 18 overlapping first stump 14 in a first overlap 22, just as for the three-part prosthesis. Leg connector segment 30, however, overlaps second stump 16 in a first connector overlap 26 and overlaps second leg segment 20 in a second connector overlap 28.

Figure 3A:
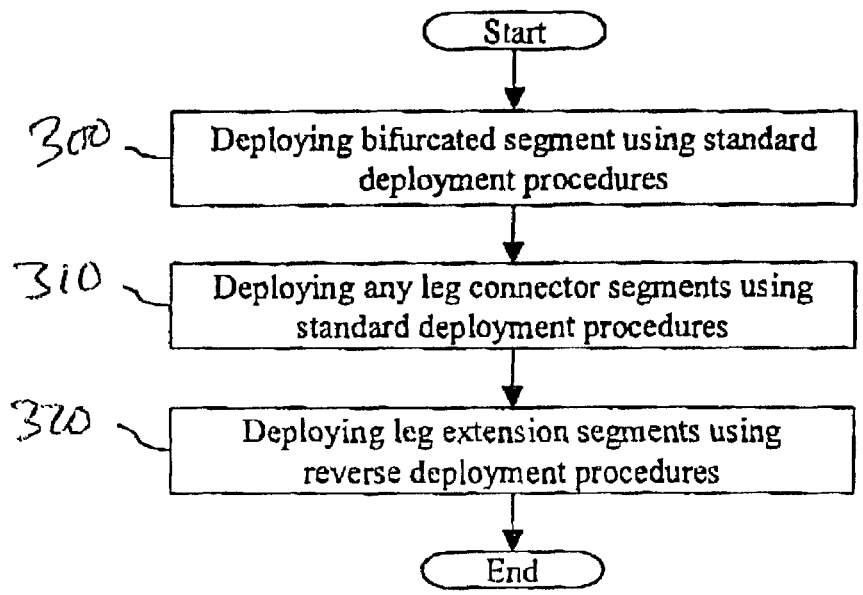
FIG. 3A depicts a flowchart of an exemplary method of this invention for deployment of a multi-part endoluminal device.
Figure 3B:
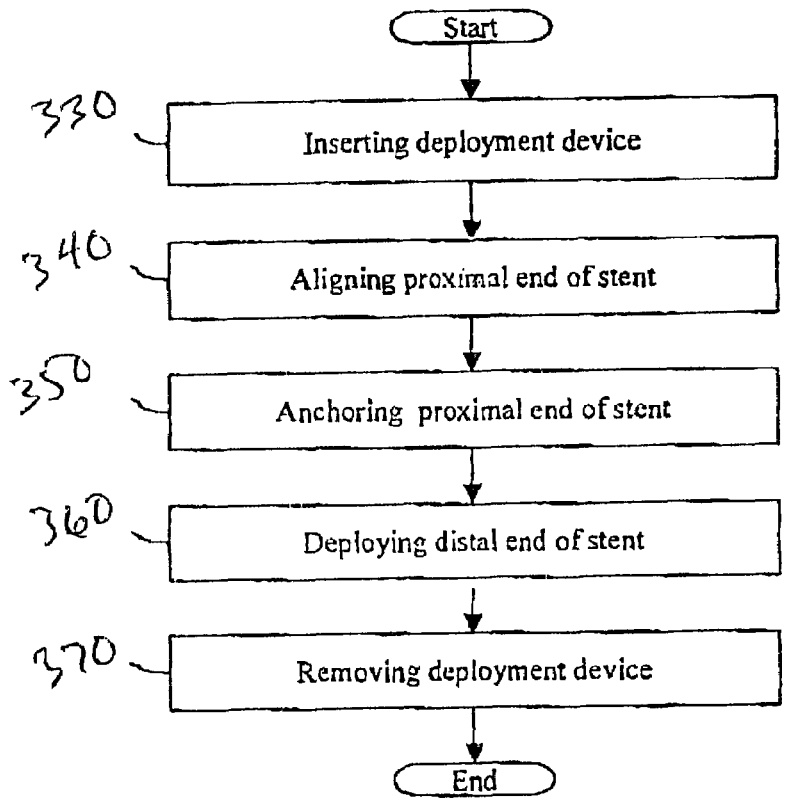
FIG. 3B depicts a flowchart of an exemplary reverse-deployment method of this invention for deployment of some components of the multi-part endoluminal device.

An exemplary method for generally deploying three-part device 9 or four-part device 19 into the configurations shown in FIGS. 1B and 2B, is depicted in the flowcharts shown in FIGS. 3A and 3B. First, as noted in step 300, bifurcated segment 10 is deployed by standard deployment procedures known in the art. The deployment is typically carried out from a vascular access site, such as a femoral artery, for deployment in a distal location such as the aorta. The access site may be percutaneously or surgically accessed, for example by surgically exposing it and puncturing it with an 18-gauge needle, as is known in the art. The standard deployment technique used in step 300 typically comprises a deployment technique that uses a standard introducer known in the art to deploy the distal end of the device first, because the distal end placement is the more critical end for placement accuracy for bifurcated segment 10. Then, in step 310, any leg connector segments, such as segment 30, are deployed also using standard, preferably distal-end-first, deployment techniques known in the art. Finally, in step 320, first and second leg segments 18 and 20, respectively, are deployed using a reverse deployment method. A general reverse deployment method is described below. This method is an exemplary one of the more specifically detailed methods described in an application titled "METHOD AND APPARATUS FOR DEPLOYMENT OF AN ENDOLUMINAL DEVICE," by Haverkost et al., U.S. patent application Ser. No. 10/081,641, filed on the same day as this application, and assigned to the common assignee of this invention, incorporated herein by reference. Other reverse deployment methods may also be used, however, such as but not limited to the method described in the patent application titled "APPARATUS AND METHOD FOR DEPLOYMENT OF AN ENDOLUMINAL DEVICE," by Johnson et al., U.S. patent application Ser. No. 10/081,636, filed on the same day as this application, and assigned to the common assignee of this application, also incorporated herein by reference.

Generally, as shown in FIG. 3B with reference to first leg segment 18 shown in FIG. 1A, the steps of reverse deployment comprise step 330 of inserting the reverse deployment introducer loaded with the device to be deployed (in this case, leg segment 18), then in step 340, aligning proximal end 19 of device 18 in a desired location. Fluoroscopic guidance and/or a guide wire may be used to guide the proximal end of the stent to the appropriate position. The desired location for device 18 is a location with the proximal end 19 positioned in the iliac, preferably just above the branch of the internal iliac artery. Proximal end 19 is anchored in step 350 and kept anchored while the remaining portion, including distal end 17, of device 18 is deployed in step 360. Then, in step 370, the introducer is removed from the lumen of the deployed device 18 and the body lumen (not shown) and is withdrawn from the access site, which may then be surgically repaired.

Anchoring step 350 may be accomplished using any mechanism that prevents significant displacement of the proximal end while the distal end is being deployed. Anchoring can be accomplished using the stent's own radial force, or by using additional anchoring means such as hooks, barbs, balloons, tethers, and notch-and-loop arrangements, many of which are discussed in application Ser. No. 10/081,641 ("the '641 application). The deployment of the remainder of the device typically involves deploying distal end 17 inside of first stump 14, preferably creating at least a 2 cm overlap 22 as shown in FIG. 2B. The extent of overlap is flexible, however, which permits all termini of the device to be accurately placed without requiring exhaustive measurements to accurately size the device. Consequently, a fewer number of stock sizes for the components of devices 9 and 19 can be manufactured that are able to fit a larger number of applications than devices known in the art for similar applications.

In one embodiment, discussed in more detail in the '641 application and later in this application, the anchoring mechanism for preventing significant displacement of the proximal end while the distal end is being deployed comprises an inflatable balloon in the retrograde portion.

In another embodiment, discussed in more detail in the '641 application, the anchoring mechanism comprises a holder in the anterograde portion. The holder may be concentrically mounted to the inner sheath and adapted to prevent distal movement of the endoluminal device during advancement of the anterograde shaft. A number of geometries and materials useful for holding a stent in place from inside the stent are described in U.S. application Ser. No. 09/574,418 by Sullivan et al., filed on May 19, 2000, assigned to the assignee of this invention, and incorporated herein by reference. For example, the holder may be a sleeve of a relatively higher friction material than the sheath over the device such that device is frictionally retained while the sheath advances. In another embodiment, the holder may comprise one or more radial protrusions that exerts an axial restraining force against individual members of device. Other structures or combinations of multiple structures may also be used as holders. A hybrid may also be provided comprising both a holder and a balloon or other anchoring means at the proximal end of the device.

In another embodiment, discussed in more detail in the '641 application, the introducer comprises the proximally retractable retrograde sheath and the medial sheath, wherein the anchoring mechanism comprises an extended portion of a proximal end of the endoluminal device and a notch in one or both of the medial sheath and the retrograde sheath for releasably confining the extended portion between the retrograde sheath and the medial sheath with the retrograde sheath in a first position and for releasing the extended portion with the retrograde sheath in a second, retracted position relative to the medial sheath.

In yet another embodiment, discussed in more detail in the '641 application, the anchoring mechanism comprises a tether attached to a proximal end of the endoluminal device. In an embodiment comprising the proximally retractable retrograde sheath and the medial sheath, the tether may be attached to one of the medial sheath, the retrograde sheath, or the inner sheath. In another embodiment, the tether may extend proximally from the device a sufficient distance to terminate outside a body lumen through which the introducer is adapted to be introduced. In such an embodiment, the medial sheath may comprise a lateral channel through which the tether extends.

Figure 4:
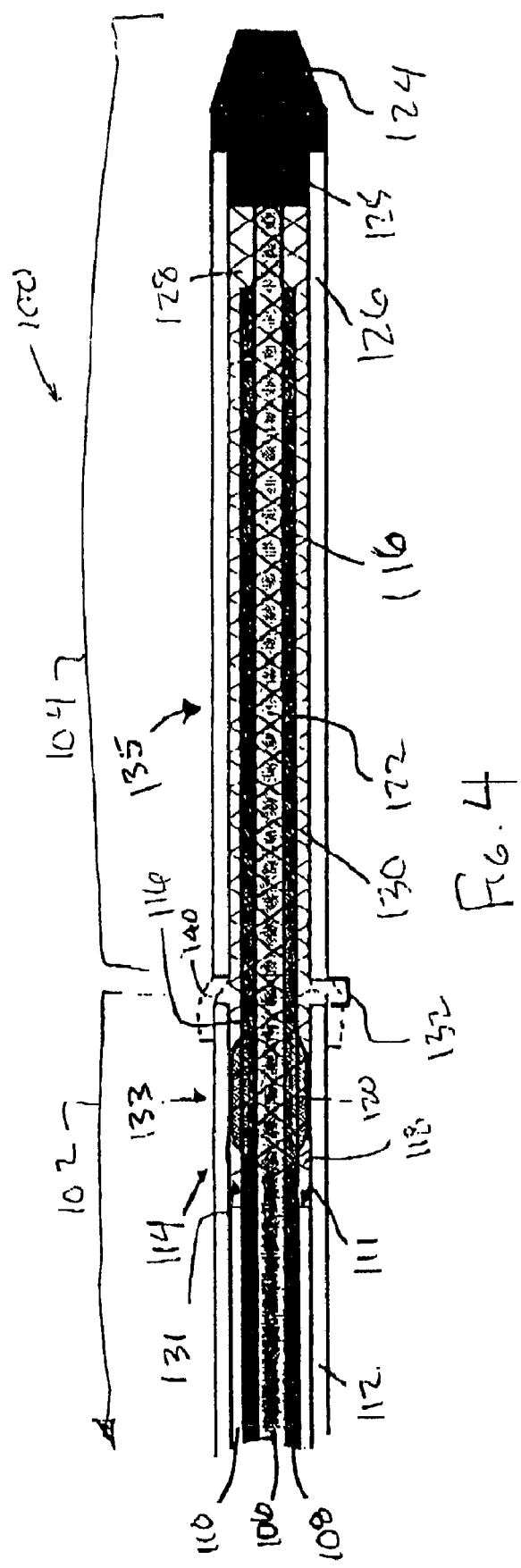
FIG. 4 is an illustration of an exemplary reverse-deployment introducer of the invention.

Referring now to FIG. 4 there is shown an exemplary introducer embodiment useful for reverse-deploying the leg segments of the prosthesis of the present invention. Introducer 100 comprises a retrograde portion 102 and an anterograde portion 104. Shaft 106 may be solid or tubular, and is surrounded by three concentrically positioned sheaths: inner sheath 108, medial sheath 110, and retrograde sheath 112. Medial sheath 110 preferably has a fixed position and operates as a radial spacer, separating retrograde sheath distal extension 114 from inner sheath distal extension 116. The distal extension 114 of retrograde sheath 112 and distal extension 116 of inner sheath 108 comprise the respective portions of those sheaths located distally of the distal end 111 of medial sheath 110.

Other types of spacers may also be used. For example, radial protrusions on inner sheath or retrograde sheath may provide such spacing. Furthermore, inner sheath may have a stepped outside diameter or retrograde sheath may have a stepped inside diameter, such as created by medial sheath being fused to either inner sheath or retrograde sheath, or by any other method that creates an equivalent structure.

Figure 7:
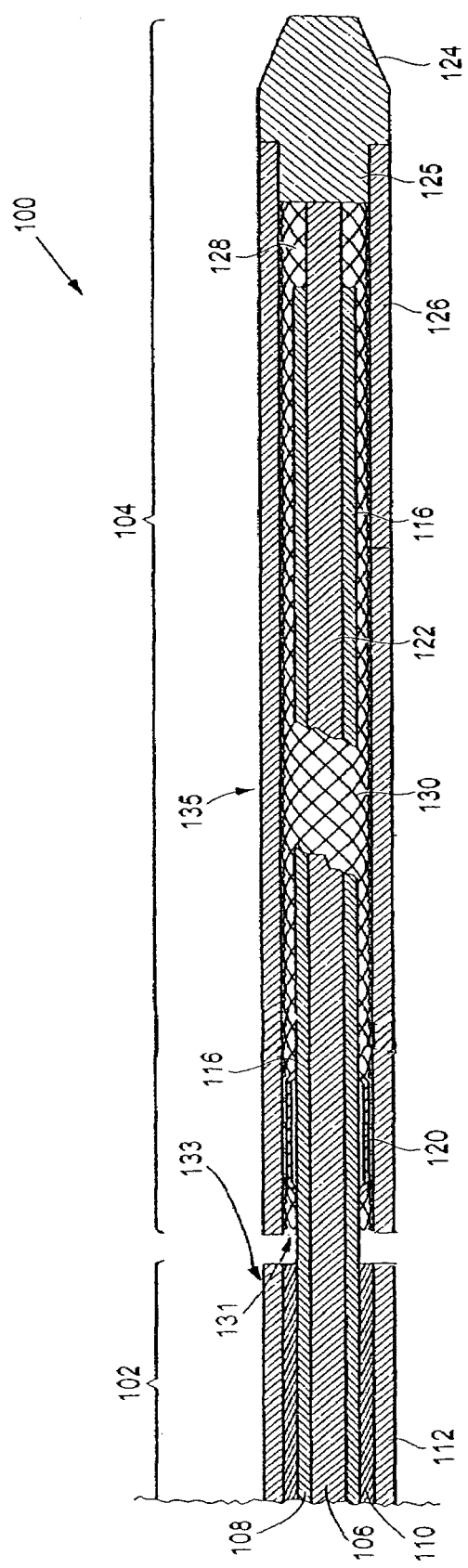
FIG. 7 is an illustration of a further exemplary embodiment of the invention.

Radial space 118 between retrograde sheath 112 and inner sheath 108 may be sufficiently large to allow room for a radial-force-exerting device, such as balloon 120. Inner sheath 108 preferably has a fixed position and may include a lumen for communicating pressurized fluid to balloon 120. Although shown in FIG. 4 with balloon 120 and proximal end 131 of device 130 as part of retrograde portion 102 covered by retrograde sheath 112, in an alternative embodiment, shown in FIG. 7, balloon 120 and proximal end 131 of device 130 may be part of anterograde portion 104 covered by anterograde sheath 126.

Anterograde portion 104 of introducer 100 includes a distal extension 122 of shaft 106 and distal extension 116 of inner sheath 108. Distal extension 122 of shaft 106 terminates with an attachment to radial spacer 125 connected to distal tip 124. Distal tip 124 is coupled to anterograde sheath 126, which extends proximally from distal tip 124, and is positioned concentrically about shaft distal extension 122 and inner sheath distal extension 116. Radial spacer 125 creates an area 128 into which an endoluminal device 130, such as leg segments 18 or 20, can be loaded.

Retrograde sheath 112 and anterograde sheath 126 may have a lateral space 132 therebetween, the sheaths may abut one another (not shown) without any space 132, or the sheaths may laterally overlap one another as depicted by dashed lines 140 in FIG. 4. Dashed lines 140 show a proximal extension of anterograde sheath 126 that overlaps retrograde sheath 112. In an alternative embodiment, a similar distal extension (not shown) of retrograde sheath 112 may laterally overlap anterograde sheath 126.

Figure 5:
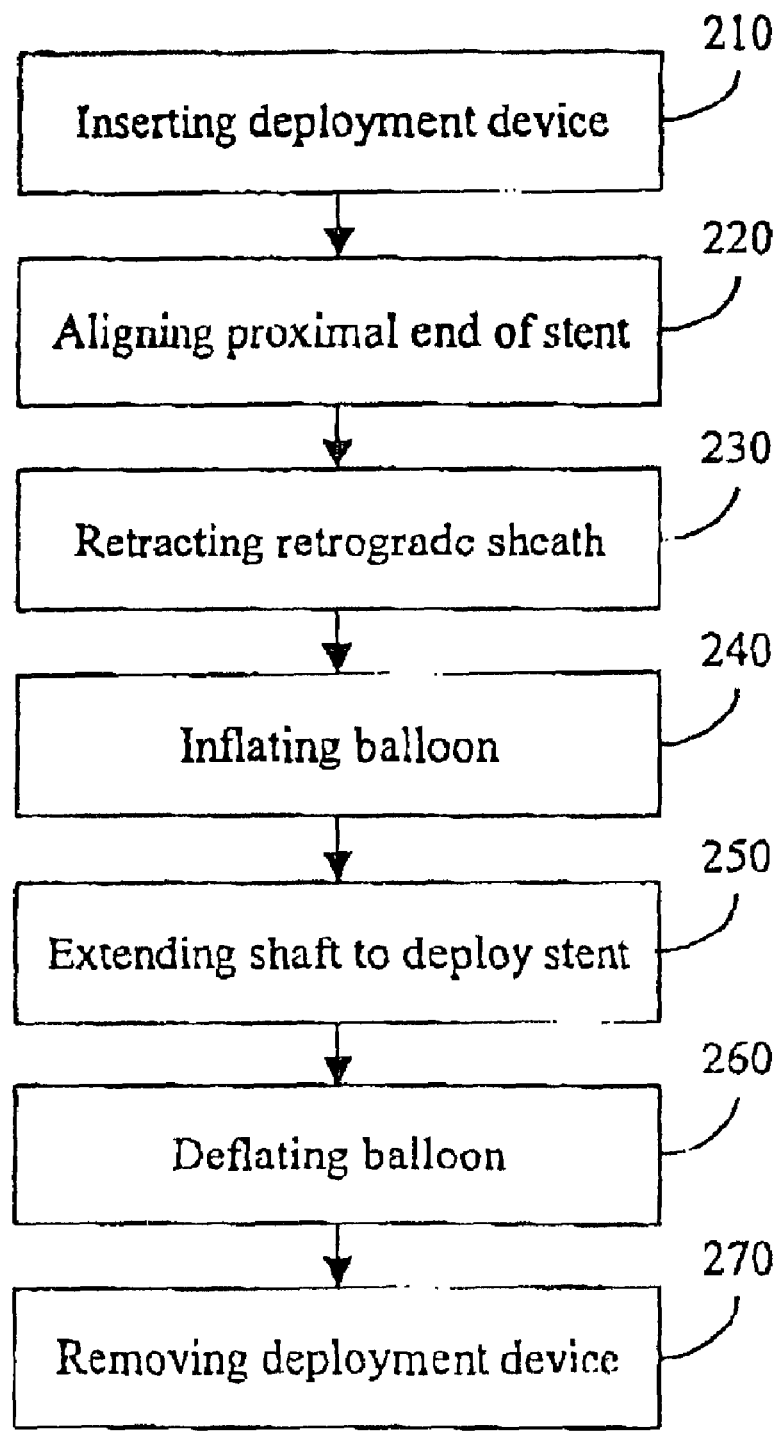
FIG. 5 depicts a flowchart of an exemplary method for reverse deployment using the introducer of FIG. 4.

An exemplary method for using introducer 100 is depicted in the flowchart shown in FIG. 5. The method may be performed, for example, in an operating room or an angiographic suite, preferably under fluoroscopic guidance as is known in the art. First, the introducer is inserted into a body lumen, as indicated in step 210, distal tip 124 first, from a proximal access site for vascular deployment. The proximal access site for deploying leg segment 18 is typically the same access site, such as a femoral artery or iliac artery, used to carry out step 300. For leg segment 20, the femoral artery or iliac artery on the other side of the body from the one used for deploying leg segment 18 may typically be used. Typically, the introducer is threaded into the lumen over a guidewire (not shown) as is well known in the art.

Next, in step 220, the proximal end 131 of endoluminal device 130 is aligned in an appropriate deployment position. Fluoroscopic guidance and/or a guide wire may be used to guide proximal end 131 into the desired position. For example, where endoluminal device 130 is an AAA stent graft, proximal end 131 of device 130 is positioned in the iliac (not shown), preferably just above a branch of the internal iliac artery (not shown).

Then, in step 230, retrograde sheath 112 is retracted at least far enough to expose proximal end 131 of device 130 and balloon 120. In an alternative embodiment wherein the proximal end 131 and balloon 120 are located under anterograde sheath 126, the anterograde sheath 126 is initially advanced far enough to expose the proximal end and balloon. Balloon 120 is inflated in step 240, such as by pressurizing balloon 120 with fluid communicated via a lumen in inner sheath 108, to exert radial force that compresses the retrograde portion 133 of device 130 against the lumen wall (not shown). In step 250, shaft 106 is extended distally to deploy the anterograde portion 135 of device 130. As used herein, the "retrograde portion" of device 130 refers to any portion initially covered by the retrograde sheath, and the "anterograde portion" refers to the remainder of the device distal of the retrograde portion. Balloon 120 is then deflated in step 260 and introducer 100 is removed from the lumen in accordance with step 270. Thus, introducer 100 and the method depicted in FIG. 3 provides means for accurately placing the proximal end of an endoluminal device.

In an alternative method, step 240 of inflating balloon 120 may be carried out prior to step 230 of retracting retrograde sheath 112, so that the balloon exerts radial force compressing retrograde portion 133 of device 130 into the retrograde sheath. Then, after step 250 of extending shaft 106 to deploy anterograde portion 135 of device 130, balloon 120 is deflated in step 260 and retrograde sheath 106 is retracted in step 230 to complete deployment of the retrograde portion of the device. Finally, the introducer is removed in step 270. Thus, in a first method, the steps are performed in numerical order as shown in FIG. 5, and in a second method, the steps are performed in the step order 210-220-240-250-260-230-270. The second method has the advantage that the balloon does not press against the lumen wall, but instead presses against the retrograde sheath, thus avoiding exertion of stress on the lumen wall. This second method is particularly desirable in the case of diseased lumen walls, which could be damaged due to the force of the balloon. This method, however, may sacrifice a few millimeters of accuracy due to recoil of the device 130. Consequently, the second method may be more desirable for applications in which the small sacrifice in accuracy is medically acceptable.

Referring now to a typical prior art introducer as seen in FIGS. 6A and 6B, there is shown a standard pre-loaded delivery system 610 comprising an outer sheath 612, a compressed endoluminal device 614 loaded therein, and a conventional stabilizer 616 loaded adjacent to the proximal end 617 of the endoluminal device. A standard deployment technique comprises maneuvering the introducer to a desired deployments location and retracting outer sheath 612 so that the endoluminal device is deployed beginning at its distal end and ending at its proximal end. Stabilizer 616 stabilizes or prevent retraction of endoluminal device 614 when sheath 612 is retracted, thus effecting deployment of the device into a desired location by forcing relative movement between the sheath and the device.

Delivery system 610 also may comprise a catheter tip 620 at its distal end attached to an internal shaft 623 that runs through the delivery system through inner lumen 622 in stabilizer 616, as shown in FIG. 6A. A stabilizer handle 626 is typically located at the proximal end of stabilizer 616, outside the body lumen. Internal shaft 623 may guide the delivery system through the body lumen over a guidewire (not shown) to the area to be repaired, or may be adapted for inflating a balloon (if applicable), and/or for flushing the system.

Other apparatus and methods for reverse deployment are described and shown in more detail in U.S. patent application Ser. No. 10/081,641 and U.S. patent application Ser. No. 10/081,636, all of which are incorporated by reference. Any of these methods, or any other methods known in the art for deployment of a device in an iliac artery by deploying the end farthest from the heart first, may be used. Furthermore, although described herein by example with respect to deployment of an AAA device, the method of this invention is not limited to deployments in a particular vascular locations, nor even to vascular applications. The method of this invention may be used for deployment of any type of multi-part endoluminal device, such as but not limited to a stent, graft, or combination thereof, in any type of body lumen.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A method for deployment of a multi-part endoluminal device in a distal location in a body lumen from a proximal location, the device having at least a first portion and a second portion, each portion having a distal end and a proximal end, the method comprising the steps of:
   (a) deploying the first portion in a body lumen by aligning the first portion distal end in a desired location and then deploying a remainder of the first portion including the first portion proximal end; and
   (b) deploying the second portion in the body lumen by aligning and anchoring the second portion proximal end in a desired location and then deploying a remainder of the second portion including the second portion distal end in overlapping engagement with the first portion proximal end, the step of deploying the second portion comprising:
   (b1) inserting an introducer into the body lumen, the introducer comprising an anterograde sheath mounted over the second portion and attached distally to a distal tip attached to a distally movable shaft extending axially through the second portion;
   (b2) aligning the introducer in a deployment location;
   (b3) extending the shaft to distally advance the anterograde sheath to deploy at least a distal section of the second portion; and
   (b4) removing the introducer from the body lumen, wherein the introducer further comprises anchoring means for anchoring a proximal section of the second portion during deployment of the second portion from a proximal end to a distal end of the second portion, the method further comprising aligning the proximal end of the second portion with the deployment location in step (b2), anchoring the proximal end prior to or during step (b3), and releasing the proximal end prior to or concurrently with step (b4).

2. The method of claim 1, wherein the first portion comprises a modular bifurcated device having a main body portion with a distal end, a first stump, and a second stump, each stump having a proximal end, and the second portion comprises at least one leg portion adapted to interface with the first stump, wherein step (a) comprises deploying the bifurcated device in a body lumen by aligning the distal end of the main body portion in a desired location and deploying the remainder of the first portion sequentially from the distal end to the first stump proximal end and second stump proximal end, and step (b) comprises deploying the leg portion with the leg portion distal end in overlapping engagement with the first stump proximal end.

3. The method of claim 2, wherein the bifurcated device is adapted to be deployed in an aorta and the leg portion is adapted to be deployed in an iliac artery.

4. The method of claim 3, wherein the desired location for the leg portion proximal end is distal of an internal iliac artery.

5. The method of claim 2, wherein the device further comprises a second leg portion having a distal end and a proximal end, the steps further comprising:
   (c) deploying the second leg portion in the body lumen by aligning and anchoring the second leg portion proximal end in a desired location and then deploying a remainder of the second leg portion including the second leg portion distal end in overlapping engagement with the second stump proximal end.

6. The method of claim 5, wherein the bifurcated device is adapted to be deployed in an aorta and the two leg portions are each adapted to be deployed in an iliac artery.

7. The method of claim 5, wherein step (a) comprises deploying the main body portion sequentially from the distal end to the proximal ends of the stumps and steps (b) and (c) comprise deploying each of the first and second leg portions sequentially from the proximal end to the distal end.

8. The method of claim 5, wherein the steps (a) and (b) are performed from a first proximal access location and step (c) is performed from a second proximal access location.

9. The method of claim 2, wherein the device further comprises a second leg portion having a distal end and a proximal end and a leg connector portion having a proximal end and a distal end and adapted to interface with the second stump and the second leg portion, the method further comprising the steps of:
   (c) deploying the leg connector portion by aligning the leg connector distal end with the second stump proximal end and then deploying a remainder of the leg connector including the leg connector proximal end; and (d) deploying the second leg portion in the body lumen by aligning and anchoring the second leg portion proximal end in a desired location and then deploying a remainder of the second leg portion including the second leg portion distal end in overlapping engagement with the leg connector proximal end.

10. The method of claim 9, wherein the steps (a) and (b) are performed from a first proximal access location and steps (c) and (d) are performed from a second proximal access location.

11. The method of claim 9, wherein steps (a) and (b) comprise deploying each of the main body portion and the leg connector sequentially from its respective distal ends to its respective proximal end or ends and steps (c) and (d) comprise deploying each of the first and second leg portions sequentially from its respective proximal end to its respective distal end.

12. The method of claim 1, comprising confining the endoluminal device between the anchoring means and the advancing anterograde sheath in step (b3).

13. The method of claim 1, wherein the anchoring means comprises an inflatable balloon and the anterograde sheath extends proximally over the balloon, in which the method further comprises in step (b3) partially advancing the anterograde sheath to expose the balloon, inflating the balloon, completing advancement of the anterograde sheath, and then deflating the balloon.

14. The method of claim 1, wherein the anchoring means comprises an inflatable balloon, and the method further comprises inflating the balloon prior to step (b3) and deflating the balloon after step (b3).

15. The method of claim 14, wherein the introducer further comprises a proximally retractable retrograde sheath mounted concentrically over the shaft and extending axially over the proximal end of the endoluminal device and the balloon, the method further comprising retracting the retrograde sheath prior to inflating the balloon, and inflating the balloon to anchor the proximal end of the endoluminal device against the body lumen.

16. The method of claim 14, wherein the introducer further comprises a proximally retractable retrograde sheath mounted concentrically over the shaft and extending axially over the proximal end of the endoluminal device and the balloon, the method further comprising inflating the balloon to anchor the proximal end of the endoluminal device against the retrograde sheath and then retracting the retrograde sheath after deflating the balloon.

17. A system for deploying a plurality of endoluminal devices, the system comprising:
a first introducer loaded with a first endoluminal device having a distal end and a proximal end, the first introducer adapted to deploy the first endoluminal device sequentially from the distal end to the proximal end; and
a second introducer loaded with a second endoluminal device having a proximal end and a distal end adapted to engage the first endoluminal device proximal end, the second introducer comprising means for anchoring the proximal end of the second endoluminal device while deploying the second endoluminal device sequentially from the proximal end to the distal end and for releasing the proximal end of the second endoluminal device after deployment thereof prior to or concurrently with the removal of the second introducer, the second introducer further comprising an anterograde sheath mounted over the second endoluminal device and attached distally to a distal tip attached to a shaft extending axially through the second endoluminal device, the shaft distally movable for advancing the anterograde sheath to unsheathe the second endoluminal device.

18. The system of claim 17, wherein the second endoluminal device distal end is adapted to be deployed radially within the first endoluminal device proximal end.

19. The system of claim 18, wherein the second endoluminal device distal end is adapted to longitudinally overlap the first endoluminal device proximal end along a length of at least about 2 centimeters.

20. The system of claim 17, wherein the first endoluminal device comprises a bifurcated device having a main body portion with a distal end, and two stumps, each stump having a proximal end, and the second endoluminal device comprises a first leg portion adapted to interface with the first stump.

21. The system of claim 17, wherein the first endoluminal device comprises a bifurcated device having a main body portion with a distal end, a first stump with a proximal end, and a second stump with a proximal end, in which the second endoluminal device comprises a first leg portion adapted to interface with the first stump, and the system further comprises a third introducer loaded with a second leg portion having a proximal end and a distal end adapted to engage the second stump proximal end, the third introducer adapted to anchor the proximal end of the second leg portion while deploying the second leg portion sequentially from the proximal end to the distal end.

22. The system of claim 21, wherein the third introducer comprises an anterograde sheath mounted over the third endoluminal device and attached distally to a distal tip attached to a shaft extending axially through the third endoluminal device, the shaft distally movable for advancing the anterograde sheath to the third endoluminal device.

23. The system of claim 17 further comprising
a third introducer loaded with a bifurcated endoluminal device having a main body portion with a distal end, a first stump with a proximal end, and a second stump with a proximal end, the third introducer adapted to deploy the main body portion sequentially from the distal end to the first and second stump proximal ends;
wherein the first endoluminal device is a leg connector adapted to interface with the first stump proximal end, and the second endoluminal device comprises a first leg portion adapted to interface with the leg connector.

24. The system of claim 23 further comprising:
a fourth introducer loaded with a second leg portion having a proximal end and a distal end adapted to engage the second stump proximal end, the fourth introducer adapted to anchor the proximal end of the second leg portion while deploying the second leg portion sequentially from the proximal end to the distal end.

25. The system of claim 24, wherein the fourth introducer comprises an anterograde sheath mounted over the fourth endoluminal device and attached distally to a distal tip attached to a shaft extending axially through the fourth endoluminal device, the shaft distally movable for advancing the anterograde sheath to unsheathe the fourth endoluminal device.

26. The system of claim 17, wherein the second introducer further comprises an inner sheath mounted concentrically over the shaft and the endoluminal device mounted concentrically over the inner sheath.

* * * * *